United States Patent [19]

Doll

[11] Patent Number: 5,313,268

[45] Date of Patent: May 17, 1994

[54] APPARATUS AND METHOD FOR TESTING THE LEVEL OF AN ITEM IN LIQUID

[75] Inventor: Robert J. Doll, Lockport, N.Y.

[73] Assignee: Richard L. Lindemuth, North Tonawanda, N.Y. ; a part interest

[21] Appl. No.: 854,240

[22] Filed: Mar. 20, 1992

[51] Int. Cl.$^5$ .................... G01N 1/14; G01N 21/59
[52] U.S. Cl. ..................... 356/435; 356/436; 356/440; 73/863.84; 73/61.48; 422/82; 436/164
[58] Field of Search ........ 356/435, 436, 440, 409–411; 73/863.84, 61.48, 64.56; 422/82; 436/53, 125, 164; 210/739, 745, 96.1, 143, 169, 138, 139, 141, 142, 198.1

[56] References Cited

U.S. PATENT DOCUMENTS

| | | | |
|---|---|---|---|
| 1,960,615 | 5/1934 | Baker | 436/125 |
| 1,977,359 | 10/1934 | Styer | 436/125 |
| 2,413,261 | 12/1946 | Stackhouse | 23/252 |
| 3,111,837 | 11/1963 | Evans et al. | 73/61.48 |
| 3,114,610 | 12/1963 | Gafford et al. | 23/255 |
| 3,712,792 | 1/1973 | Lyshkow | 23/254 R |
| 4,009,617 | 3/1977 | Johnson | 73/863.84 |
| 4,016,079 | 4/1977 | Severin | 356/411 |
| 4,797,000 | 1/1989 | Curtis | 356/435 |
| 4,856,906 | 8/1989 | Sunstein et al. | 356/435 |
| 4,950,610 | 8/1990 | Tittle | 436/163 |

Primary Examiner—Neil McCarthy
Attorney, Agent, or Firm—Joseph P. Gastel

[57] ABSTRACT

Apparatus for measuring the level of an item in a liquid including first and second light transmitting cylinders, a first piston and an associated conduit for conducting liquid to the first cylinder, a second piston and an associated conduit for conducting liquid to the second cylinder, a third piston and an associated conduit for conducting indicator solution to the second cylinder, a light source for transmitting light through the first and second cylinders, and a detector for measuring the difference in light transmissibility of the liquids in the first and second cylinders and providing an output depending thereon. A method of testing the level of an item in a liquid including the steps of providing a first sample of the liquid containing the item, providing a second sample of the liquid with a measured amount of indicator solution therein, comparing the light transmissibility of the first and second samples, and providing an output which is a measurement of the level of the item in the liquid.

6 Claims, 2 Drawing Sheets

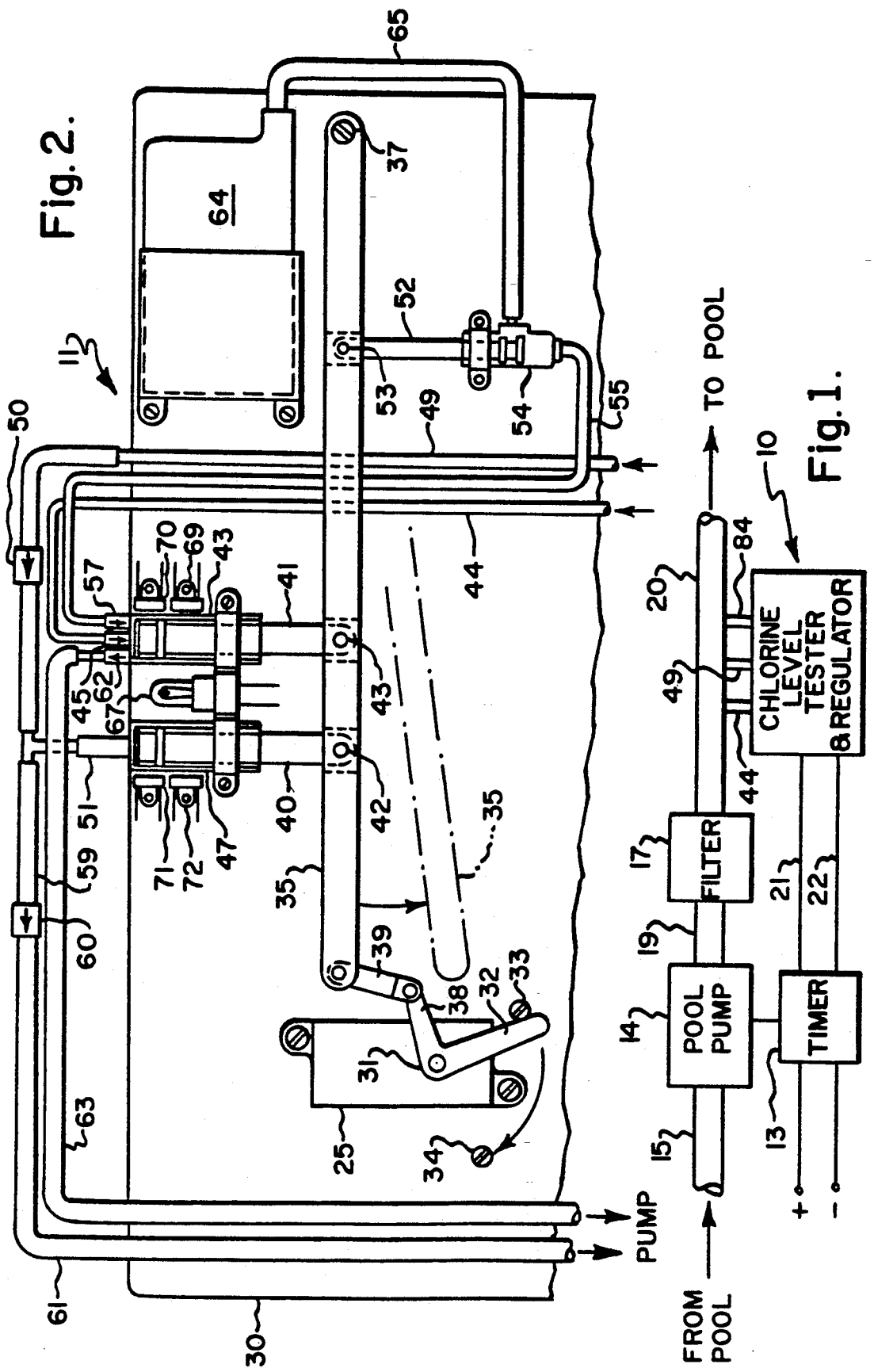

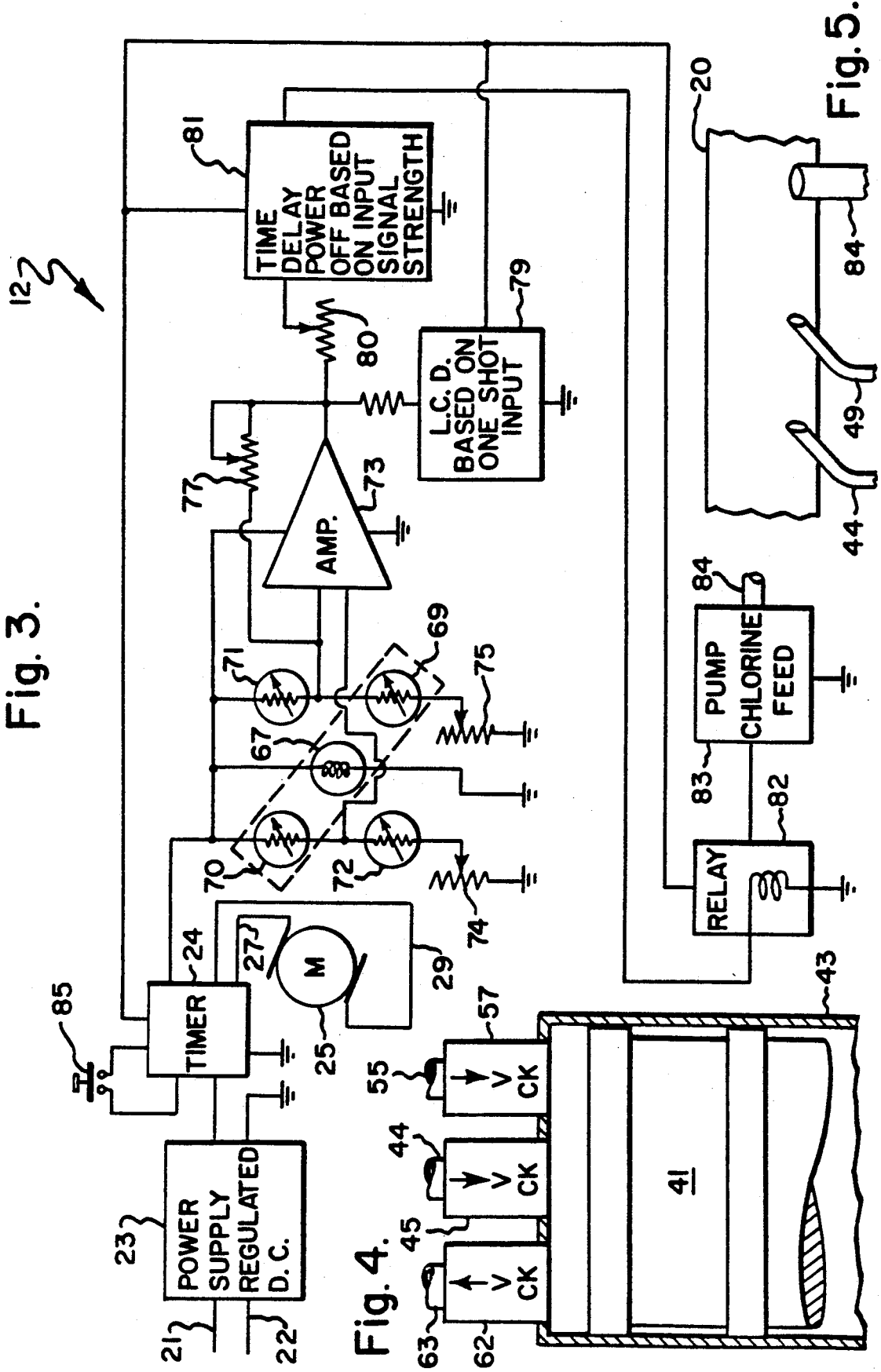

5,313,268

APPARATUS AND METHOD FOR TESTING THE LEVEL OF AN ITEM IN LIQUID

BACKGROUND OF THE INVENTION

The present invention relates to an apparatus and a method for measuring the level of an item in a liquid and more particularly for measuring the chlorine level in swimming pool water.

By way of background, there are different systems in existence for adding indicating solutions to liquids and thereafter measuring the level of an item in the liquid. However, insofar as known, prior systems were relatively complex or could not provide an accurate output based solely on adding a measured amount of indicating solution to a single sample.

SUMMARY OF THE INVENTION

It is accordingly one object of the present invention to provide an improved electromechanical apparatus for measuring the amount of an item in a liquid by automatically adding an indicator solution to the liquid and comparing the light transmissibility of such solution with liquid which does not contain the indicator solution.

Another object of the present invention is to provide an improved method for measuring the level of an item in a liquid, and more particularly, for measuring the level of chlorine in pool water. Other objects and attendant advantages of the present invention will readily be perceived hereafter.

The present invention relates to apparatus for measuring the level of an item in a liquid comprising first means for placing said liquid into a first light-transmitting vessel, second means for placing said liquid plus an indicator solution into a second light-transmitting vessel, third means for passing a light of a predetermined color through said first and second vessels, and detector means for detecting the differences in light transmission of said liquids in said first and second vessels and for producing an output based thereon which is indicative of the level of said item in said liquid.

The present invention also relates to a method of testing the level of an item in a liquid comprising the steps of providing a first sample of the liquid containing the item, providing a second sample of the liquid with a measured amount of indicator solution therein, comparing the light transmissibility of said first and second samples, and providing an output which is a measurement of the level of said item in said liquid.

The various aspects of the present invention will be more fully understood when the following portions of the specification are read in conjunction with the accompanying drawings wherein:

BRIEF DESCRIPTION OF THE DRAWINGS

FIG. 1 is a fragmentary schematic view of an improved automatic chlorine level tester and regulator incorporated into the water pumping system of a swimming pool;

FIG. 2 is a fragmentary side elevational view primarily of the mechanical portion of the improved chlorine level tester and regulator;

FIG. 3 is a schematic electrical diagram of the improved chlorine level tester and regulator;

FIG. 4 is an enlarged fragmentary view of a portion of FIG. 2; and

FIG. 5 is a fragmentary enlarged detail view of a portion of FIG. 1.

DESCRIPTION OF THE PREFERRED EMBODIMENTS

While the following description is directed primarily to the use of the present invention for testing and regulating the chlorine level in swimming pool water, it will be appreciated that it can be used or modified to test other characteristics of water, including but not limited to the bromine level, pH and iron level.

Relative to the chlorine aspect of the present invention, summarizing briefly in advance, the chlorine level tester and regulator 10 is for installation in the water circulation circuit of a swimming pool. Tester and regulator 10 (FIG. 1) includes a combined mechanical and hydraulic component 11 (FIG. 2) and an electrical control component 12 (FIG. 3) with portions of the latter also being shown in FIG. 2. The tester and regulator 10 is designed to operate automatically during the filtration cycle of a swimming pool, or it can be actuated manually. The filtration cycle of the pool is initiated by a timer 13, which is connected to a suitable source of electrical current. Timer 13 periodically activates a pool pump 14 which receives pool water from conduit 15 and pumps it to pool filter 17 through conduit 19 and the water then passes back to the pool through conduit 20, as is well known.

The tester and regulator 10 of the present invention is automatically actuated in response to the energization of filtration cycle timer 13. The electrical power for the chlorine level tester and regulator 10 (hereafter referred to as tester) is obtained through electrical leads 21 and 22 coming from the timer 13, and, more specifically, leads 21 and 22 energize a suitable rectification system 23 (FIG. 3) which produces a regulated DC output. As soon as the power supply 23 is energized, a suitable timer 24, which is coupled thereto, is also energized. In the specific embodiment shown, the timer energizes motor 25, which is connected thereto by leads 27 and 29, after the timer 24 has been energized for fifteen minutes. This fifteen minute waiting period insures that the tester 10 will not be activated until the pool water passing through conduit 20 provides a fair representation of the chlorine level of the pool water.

Motor 25 is mounted on a board 30 with other components of the system. When motor 25 is energized, it will move bellcrank lever 31 in a clockwise direction so that arm 32 will move away from stop 33 and move to stop 34 and remain there for two seconds. In response to the movement of lever 31, lever 35, which is pivoted to board 30 at 37, will move to its dotted line position 35 because of its connection to lever arm 38 through link 39. When lever 35 moves to its dotted line position, pistons 40 and 41, which are pivotally connected to it at pivots 42 and 43, respectively, will move downwardly. A precise amount of pool water will be drawn into semi-transparent cylinder 43 through conduit 44 and check valve 45 by piston 41. Pool water will also be drawn into semi-transparent cylinder 47 by piston 40 from conduit 20 via conduit 49, check valve 50 and conduit 51. Also during the initial movement of lever 35 to its dotted line position, piston 52, which is pivotally connected to lever 35 at 53, will be moved downwardly to expel a precise amount of chlorine indicating solution from cylinder 54 into conduit 55 which is in communication with cylinder 43 via check valve 57. Thus, during the two-second dwell of lever arm 32 at stop 34, a precise amount of pool water is sucked into both cylinders 43 and 47, and, additionally, a precise amount of chlorine indicating solution is expelled from cylinder 54 and injected into cylinder 43. During the foregoing action of pistons 40, 41 and 52, the conduits leading to cylinders 43 and 47 are full of liquid to insure that precise amounts of all of the liquids are supplied to cylinders 43 and 47.

After the foregoing two-second dwell, the timer 24 and associated contacts therein cause reversal of motor 25 to cause bellcrank lever 31 to return to its position of FIG. 2, whereby lever 35 returns to its solid line position. Thus, pistons 40 and 41 will return to their positions of FIG. 2. Pool water will thus be expelled from cylinder 47 and then be dumped to a suitable location via conduits 51 and 59, check valve 60 and conduit 61. Also, the liquid will be expelled from cylinder 43 via check valve 62 and conduit 63 and dumped to a suitable location. At this time piston 52 will also be raised to its solid line position in cylinder 54, and thus a precisely measured charge of chlorine indicating solution will be drawn into cylinder 54 from tank 64 via conduit 65. The foregoing discharging of liquid from cylinders 43 and 47 is for the purpose of flushing to assure that they are cleaned out so that any liquid which they subsequently draw to be tested is a fair representation of the pool water at that time.

Check valves 45, 57 and 62 should be as close as possible to the cylinder 43 so that there will be practically no liquid left in cylinder 43 when piston 41 is in its uppermost position, thereby assuring the accuracy of the measurements because each new charge of liquid is not mixed with a significant amount of residual liquid from a previous filling.

Lever 35 will be maintained in its solid line position for two seconds, and thereafter timer 24 will cause a cycle to be repeated wherein motor 25 causes lever 35 to move to its dotted line position for two seconds to draw in clear pool water into cylinder 47 through the above described path and to draw in a mixture of a precise measured amount of chlorinated pool water and a precise measured amount of chlorine indicating solution into cylinder 43 through the above-described path. While a precise measured amount of chlorinated pool water is also drawn into cylinder 47, this precision is not critical to the subsequent measurement of the chlorine level. Motor 25 is then turned off by timer 24.

From FIG. 5 it can be seen that the ends of conduits 44 and 49 in conduit 20 essentially comprise Venturis so that water from conduit 20 will not be forced into these conduits as a result of the action of the pool pump 14. Water will only enter conduits 44 and 49 as a result of the operation of the pistons 40 and 41 when the tester 10 is actuated in the above-described manner. Alternately, normally closed solenoid valves may be installed in conduits 44 and 49, and these will be opened only in response to the energization of tester 10.

The timer 24 then activates the electrical measuring circuit of FIG. 3. In this respect, current is supplied to blue lamp 67, which may be a blue light emitting diode manufactured by Industrial Devices, Inc., which provides a blue light which shines through semi-transparent cylinder 43 onto photocells 69 and 70 and through semi-transparent cylinder 47 onto photocells 71 and 72. The photocells 69, 70, 71 and 72 are in a Wheatstone bridge type of circuit with amplifier 73. The photocells are of the cadmium sulfide type to respond to the wave length of the light transmitted through the solution.

Variable resistors 74 and 75 are used to balance the legs of the circuit in which they are located. This balancing is effected with unchlorinated water in cylinders 43 and 47 prior to operating the system. Variable resistor 77 is used to calibrate the LCD 79 which is responsive to a one-shot input therein. A meter can be used instead of an LCD, if desired. Variable resistor 80 is utilized to vary the input signal strength to time delay unit 81, to increase or decrease the duration of time delay provided by the time delay unit 81. As noted hereafter, the time delay determines the amount of chlorine which is added to the pool water.

As noted above, cylinder 47 contains chlorinated pool water and cylinder 43 contains a mixture of a precise amount of chlorinated pool water plus a precise amount of chlorine indicating agent which in this instance is ortholidine and hydrochloric acid. The chlorinated pool water, without the indicator solution therein, varies in light transmissibility because of the amount of foreign matter therein, which is usually solid material which the filter 17 does not remove. The voltage drop across photocells 71 and 72 will therefore vary with the light they receive from lamp 67, which in turn depends on the amount of unfiltered foreign matter in the pool water. The greater the amount of foreign matter, the higher will be the resistance provided by photocells 71 and 72. However, since the same pool water is in both cylinders 43 and 47, the clarity of the pool water will not affect the voltage output to amplifier 73. In other words, the voltage drop across each of photocells 69, 70, 71 and 72 due to the foreign matter in the pool water will be the same so that the differences in clarity of pool water will not affect the output to amplifier 73.

As can be seen from FIG. 2, photocells 69 and 70 will receive less light than photocells 71 and 72 because the light transmission of liquid containing the chlorine indicating solution in cylinder 43 will be less than the light transmission through the chlorinated pool water in cylinder 47. This will cause a greater resistance of photocells 69 and 70 which, in turn, will cause an unbalance of the Wheatstone bridge. The amount of unbalance of the Wheatstone bridge is proportional to the amount of chlorine in the pool water which will be reflected as a voltage output from the Wheatstone bridge to amplifier 73, and this output in turn will be transmitted to time delay unit 81. In other words, the greater the amount of chlorine in the pool water, the greater will be the voltage output to amplifier 73. It is to be noted that because of the orientation of photcells 69 and 70 in the legs of the Wheatstone bridge, the voltage drop to amplifier 73 will be double as compared to the voltage drop obtained if only a single one of the photocells 69 and 70 was present. Amplifier 73 may be a No. 740 OP-AMP distributed by Radio Shack. Time delay unit 81 may be of any desired type. After two seconds the timer 24 turns power off to the blue light 67 and all of the photocells and the amplifier 73.

Based on the level of the signal received by the time delay unit 81, the latter will energize relay 82 for an inversely proportionate period of time which in turn will actuate chlorine feed pump 83 for that period of time, and the latter having a predetermined pumping cavity will provide a predetermined amount of chlorine to the pool through conduit 84 depending on the length of time for which the pump 83 is actuated. In the foregoing respect, the greater the voltage output from amplifier 73, the less will be the time delay from time delay unit 81 and the less will be the length of time of operation of pump 83.

The timer 24 will maintain power to the time delay 81 for approximately ten minutes. Time delay 81 in turn energizes relay 82 for up to 10 minutes, and then timer 24 will reverse the power to motor 25 to cause it to move back to its solid line position of FIG. 2. After two seconds, timer 24 shuts off all power to the electrical circuit of FIG. 3 and the timer will again be reset to produce the foregoing entire cycle when the filter pump is again turned on by the timer 13 as described above.

A manual switch 85 is associated with timer 24 to energize the circuit of FIG. 3 when it is desired to energize the chlorine level tester and regulator at will without having it operate in response to the actuation of the pool pump filter system as described above.

In a model of the above-described circuit of FIG. 3, the parts had the following approximate values and resistors 69, 70, 71 and 72 had the following approximate values when the blue light was energized and when there was clear water in cylinders 43 and 47:

| Part Resistor | Value Ohms |
| --- | --- |
| 69 | 2.4K |
| 70 | 2.6K |
| 71 | 2.1K |
| 72 | 4.2K |
| 74 | 0–12K |
| 75 | 0–12K |
| 77 | 0–10K |
| 80 | 0–10K |

The voltage supply is 18 volts. Cylinders 43 and 47 had volumes of approximately one cubic centimeter. The amount of indicator solution injected into cylinder 43 was approximately 0.06 cubic centimeters. The indication solution specifically was 0.1% OTO (contains ortholidine 0.1% and hydrochlorine acid 3.7%).

The above-described circuit having the above values was tested and provides the following results:

| Voltage output to amplifier 73 | Chlorine level in parts per million |
| --- | --- |
| .28 | .4 |
| .40 | .6 |
| .55 | 1.0 |
| .70 | 1.5 |
| .80 | 2.0 |
| 1.10 | 4.0 |
| 1.50 | 5.0 |

While the above description has been directed to measuring the level of chlorine in swimming pool water, it will be appreciated that the same apparatus and procedure may be used with measuring other aspects of water chemistry such as bromine, pH and iron by the use of other suitable indicators and suitably colored lamps. When bromine is being tested, the above described circuit and the same indicator solution can be used as with chlorine.

The above circuit was also used to test pH. However, the indicator solution which was used was phenol red, and the lamp which was used was blue, as described above. The phenol red was the type marketed by Poolmaster, Inc. The following results were obtained from a test:

| Voltage output to amplifier 73 | pH |
| --- | --- |
| .8 | 7.8 |
| .65 | 7.4 |
| .5 | 7.0 |
| .25 | less than 7.0 |

The above circuit was also used to test the concentration of dissolved iron. An "Iron Test Reagent" is used which is distributed by Biolab Inc. of Decatur, Ga. In this test a blue colored lamp was also used, as described above. The following results were obtained from a test:

| Voltage output to amplifier 73 | Iron in PPM |
| --- | --- |
| .85 | 1.0 |
| 1.20 | 3.0 |
| 2.75 | 5.5 |

As noted above, a blue light was used for the above tests. However, it will be appreciated that lamps of other colors can also be used. The color of the lamp which is selected may be based on the spectrum of light that is most absorbed by the compounds in the cylinder as a result of mixing the reagent with the water to be tested. Generally one or more spectra of light will be absorbed to produce a color change.

While specific times have been set forth above in describing the cycles of operation, it will be appreciated that they are merely by way of example and not of limitation.

While preferred embodiments of the present invention have been disclosed, it will be appreciated that it is not limited thereto but may be embodied within the scope of the following claims.

What is claimed is:

1. Apparatus for measuring the level of an item in a liquid comprising first and second light-transmitting cylinders, first and second pistons associated with said first and second cylinders, respectively, a third cylinder, a third piston associated with said third cylinder, lever means, means coupling said first and second and third pistons to said lever means, first and second conduit means in communication with said first and second cylinders, respectively, a source of indicator solution, third conduit means for effecting communication between said second and third cylinders, fourth conduit means for effecting communication between said source of indicator solution and said third cylinder, motor means for actuating said lever means to cause said first and second pistons to draw liquid into said first and second cylinders, respectively, through said first and second conduit means, respectively, and for causing said third piston to eject indicator solution into said second cylinder through said third conduit means, and for causing said first and second pistons to eject said liquid and a mixture of said liquid and indicator solution from said first and second cylinders, respectively, and for causing said third piston to draw indicator solution into said third cylinder through said fourth conduit means from said source of indicator solution, light source means for transmitting light through said first and second cylinders, and detector circuit means for providing an output based on the different light transmissions through solutions in said first and second cylinders.

2. Apparatus as set forth in claim 1 wherein said liquid is water in a swimming pool, and wherein said item is chlorine, and means for supplying chlorine to said pool in response to said output.

3. Apparatus as set forth in claim 1 wherein said detector circuit means comprises a Wheatstone bridge.

4. Apparatus as set forth in claim 1 including timer means for selectively actuating said apparatus.

5. Apparatus as set forth in claim 1 including first valve means in said second conduit means for permitting flow of said liquid into said second cylinder but preventing flow of liquid plus indicator solution from said second cylinder into said second conduit means, and second valve means in said third conduit means for permitting flow of said indicator solution from said third conduit means into said second cylinder but preventing flow of said liquid plus indicator solution from said second cylinder into said third conduit means.

6. Apparatus as set forth in claim 5 including fifth conduit means for conducting liquid from said first cylinder and for conducting liquid plus indicator solution from said second cylinder, and third valve means in said fifth conduit means for permitting flow from said first and second cylinders into said fifth conduit means but preventing flow from said fifth conduit means back into said first and second cylinders.

* * * * *